United States Patent
Robinson et al.

[11] Patent Number: 5,861,940
[45] Date of Patent: Jan. 19, 1999

[54] EYE DETECTION SYSTEM FOR PROVIDING EYE GAZE TRACKING

[75] Inventors: Michael Geraint Robinson; Craig Tombling, both of Oxfordshire; Nicholas Mayhew, Oxford; Robert George Watling Brown, Oxfordshire, all of United Kingdom

[73] Assignee: Sharp Kabushiki Kaisha, Osaka, Japan

[21] Appl. No.: 902,751

[22] Filed: Jul. 30, 1997

[30] Foreign Application Priority Data

Aug. 1, 1996 [GB] United Kingdom .................. 9616190

[51] Int. Cl.⁶ ............................................. A61B 3/10
[52] U.S. Cl. ......................... 351/221; 351/205; 351/211
[58] Field of Search .................... 351/221, 210, 351/209, 211, 205, 200, 246

[56] References Cited

U.S. PATENT DOCUMENTS

| | | | |
|---|---|---|---|
| 3,712,716 | 1/1973 | Cornsweet et al. | 351/7 |
| 5,430,509 | 7/1995 | Kobayashi | 351/221 |

FOREIGN PATENT DOCUMENTS

| | | |
|---|---|---|
| 0547599 | 6/1993 | European Pat. Off. |
| 9203088 | 3/1992 | WIPO . |
| 9205736 | 4/1992 | WIPO . |
| 9418883 | 9/1994 | WIPO . |
| 9522925 | 8/1995 | WIPO . |

OTHER PUBLICATIONS

T.E. Hutchinson et al., IEEE Transaction on System, Man, and Cybernetics, vol. 19, No. 6. pp. 1527–1533, 1989, "Human–Computer Interaction Using Eye–Gaze Input".

Y. Ebisawa, IMTC '94, pp. 963–966, 1994, "Improved Video–Based Eye–Gaze Detection Method".

K. P. White, Jr. et al., IEEE Transaction on Systems, Man, and Cybernetics, vol. 23, No. 4, pp. 1162–1168, 1993, "Spatially Dynamic Calibration Of An Eye–Tracking System".

A. Gee et al., IEEE 1994, pp. 1–6, 1994, "Non–Intrusive Gaze Tracking For Human–Computer Interaction".

*Primary Examiner*—Hung Xuan Dang

[57] ABSTRACT

An eye detection system comprises a source, such as an infrared laser diodes for emitting a divergent beam of infrared radiation. A spatial light modulator is controlled so as to act as a deflector for scanning the beam. A detector detects radiation which is retro-reflected by the eye back along the path of the scanning beam. The deflection angle of the SLM and, for a position sensitive detector, the location of the center of illumination on the detector can be used to determine the angle to the center of the pupil of the eye. By subsequently detecting the angle to the glints corresponding to other sources and, the gaze position of the eye on a screen can be determined.

26 Claims, 6 Drawing Sheets

FIG 3

EYE DETECTION SYSTEM FOR PROVIDING EYE GAZE TRACKING

TECHNICAL FIELD OF THE INVENTION

The present invention relates to an eye detection system. Such a system may be used in an eye gaze tracking system for detecting the region on a screen, such as a computer screen, at which an observer is gazing.

BACKGROUND OF THE INVENTION

Known eye gaze detection systems are disclosed in:

"Human-Computer Interaction Using Eye-gaze input", T.E. Hutchison et al, IEEE Trans. Sys., Man, Cybern., vol. 19, p.1527, 1989;

"Improved video-based eye-gaze detection method", Y. Ebisawa, Proc. IMTC '94 pp. 963–966, 1994;

K.P. White Jr., T.E. Hutchison, and J.M. Carley, Spatially dynamic calibration of an eye-tacking system, IEEE Trans. Syst., Man, Cybern., vol.23 pp. 1162–68, 1993;

A. Gee and R. Cipollo, Non-intrusive gaze tracking for human-computer interaction, Proc. Mech. Mach. Vis. 1994.

Two reflections from the eye are detected, The first is caused by the light passing through the pupil of the eye and being reflected back from the retina. The second, known as "glint" is formed by light reflected from the surface of the cornea. By, for instance, detecting the reflection from the cornea for one source and detecting the glint for several sources of illumination, the position of the eye and its direction of gaze can be calculated.

In such systems, the region in front of a screen which is likely to be occupied by the face of an observer is illuminated, for instance by an infrared light emitting diode. A two dimensional image of the observer face is then captured by a video camera, for instance based on a charge coupled device. The image is then subjected to complex image processing in order to detect the reflection of the light source from the eye.

Arrangements of this type have several disadvantages. For instance, relatively complex image processing is required in order to identify the observer eye. This requires substantial processing capability which in turn requires relatively powerful data processors and/or relatively long processing times. Further, the resolution of detection of the various reflections is limited by the resolution of the video camera. The video camera is required to capture a 2D image of the region of space which may be occupied by the observer so that the reflections which are required to be detected occupy a relatively small portion of the captured image. For video cameras of the charge coupled device (CCD) type, the size of the reflections in the image can become comparable to the intrinsic resolution of the camera. Typically, the whole face of the observer is imaged onto the CCD so that the eyes of the observer are imaged onto a relatively small proportion of the light sensitive surface of the CCD. The CCD has a finite resolution which thus limits the accuracy with which the locations of reflections can be determined. Further, the quality of the light source is an important factor in the accuracy of determination.

SUMMARY OF THE INVENTION

According to the invention, there is provided an eye detection system comprising a light source for emitting an incident beam of optical radiation, a controllable deflector disposed in the path of the incident beam for producing a scanning beam, and a detector for detecting radiation reflected by an eye back along the path of the scanning beam.

The deflector may comprise a controllable diffractive element. The deflector may comprise a spatial optical modulator. The deflector may further comprise a modulator controller for writing in the modulator and array of A×B substantially identical patterns, each of which comprises an array of C×D picture elements, where A, B, C and D are integers. The modulator controller may be arranged to select each of the identical patterns from (C×D) different patterns for deflecting the scanning beam in (C×D) different directions. Each of the different patterns may be arranged to produce divergence in the scanning beam. The source may be arranged to illuminate an array of C×D picture elements of the modulator with the incident beam.

The detector may be arranged to receive radiation deflected back towards the source by the deflector. There may be provided a beam splitter for directing radiation from the source to the deflector and for directing radiation from the deflector to the detector. The detector may comprise a detecting device disposed at the focus of a focusing optical system. The detecting device may comprise a position sensitive detector. The focusing optical system may comprise a converging lens.

The source may be arranged to produce a divergent incident beam.

The source may comprise a laser. The laser may comprise a laser diode. The laser may cooperate with a collimator and an aperture to produce the divergent incident beam.

There may be provided a scanning controller for causing the deflector to scan the scanning beam until the detector detects reflection from an eye. The scanning controller may be arranged, after detection of reflection from the eye, substantially to centre a centre of reflection from the eye in the scanning beam or with respect to the detector.

There may be provided at least one further source of optical radiation disposed remotely from the deflector. The or each further course may be arranged to admit a divergent beam. The or each further source may comprise a laser. The or each laser may comprise a laser diode. The or each laser diode may cooperate with a collimator and an aperture to produce the divergent beam. There may be provided a source controller for illuminating the source and the or each further source in sequence. The source controller may be arranged to illuminate each of the source and the or each further source following detection by the detector of reflection from the eye of optical radiation from a previously illuminated one of the source and the or each further source. There may be provided a data processor for cooperating with the detector and the deflector to determine, from the angle between a predetermined direction and the direction from the deflector to the point of reflection at the eye of each of the source and the or each further source, the eye gaze point on a surface in front of the eye.

It is thus possible to provide a system which may be used for eye gaze detection and which has improved accuracy, higher optical efficiency and lower computational requirements than for known systems. By scanning the region which an observer may occupy and then illuminating only the region of an observer eye, the available resolution of the system is concentrated into what is effectively only a relatively small portion of the 2D image formed in known systems. Thus, reflection features are much larger within the image, leading to intrinsically improved resolution. Accuracy is determined by accuracy of beam scanning, optionally improved by the use of a position sensitive detector. This represents a substantial increase in accuracy compared with known systems. Image recognition techniques are not required so that data processing requirements are simplified.

BRIEF DESCRIPTION OF THE DRAWINGS

The invention will be further described, by way of example, with reference to the accompanying drawings, in which:

FIG. 1 shows the general arrangement of an eye gaze tracking system forming part of a computer terminal containing a computer screen 1. An infrared laser 2 supplies an output infrared beam which is collimated and apertured so as to be divergent. The infrared beam is reflected from a beam splitter 3 onto a spatial light modulator (SLM) 4. The SLM 4 is controlled so as to form patterns which diffract the beam in the desired directions so that the SLM 4 acts as a beam deflector for scanning the output beam 5 throughout a region which may be occupied by an observer eye in front of the screen 1.

DETAILED DESCRIPTION OF THE INVENTION

Figure 1:
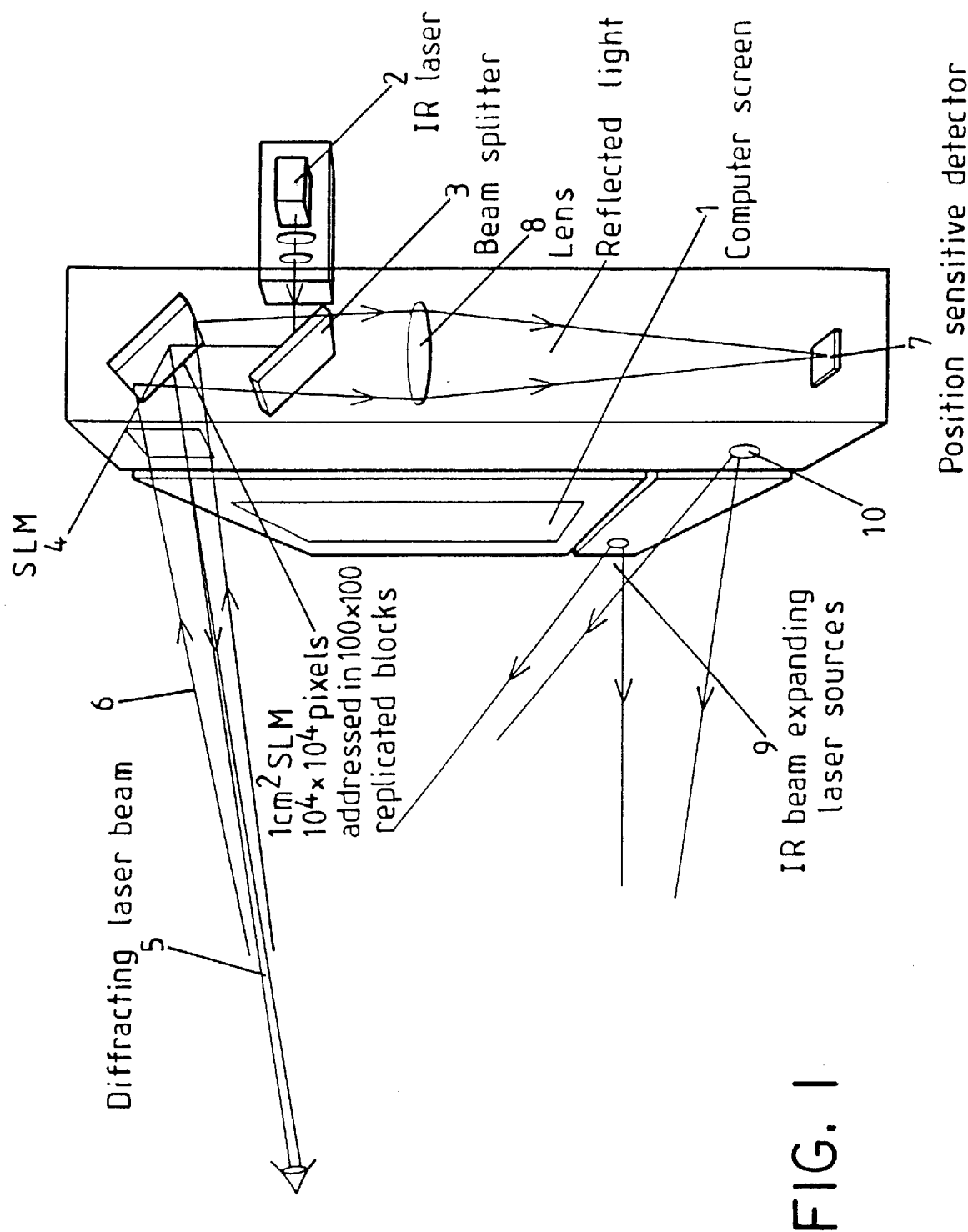
FIG. 1 is a schematic view of an eye gaze tracking system constituting an embodiment of the present invention.

When an eye of an observer is illuminated by the scanning beam 5, reflection takes place at the retina so that the eye acts as a retro-reflector returning a divergent beam 6 along the path of the illuminating beam 5. The returned beam 6 is reflected by the SLM 4 and passes through the beam splitter 3. A position sensitive detector 7 is located in the focal plain of a converging lens 8. The returned beam is thus imaged onto the position sensitive detector 7 which, in combination with the known deflection provided by the SLM 4, determines the vector from the SLM 4 to the centre of the iris of the eye.

The system shown in FIG. 1 further comprises sources, such as lasers or light emitting diodes, of expanding infrared beams shown at 9 and 10. As described in more detail hereinafter, the laser 2 is used initially to locate the eye and determine the vector passing through the centre of the iris. The laser 2 is then extinguished and the sources 9 and 10 are illuminated in turn so as to determine, by the position of the reflected light on the position sensitive detector 7, the vector from the SLM to the glint for each of the sources 9 and 10 in turn. This information may then be used to determine the region of the screen I at which the observer is gazing, for instance so as to locate a cursor at that position on the screen without requiring the use of a mouse.

Figure 2:
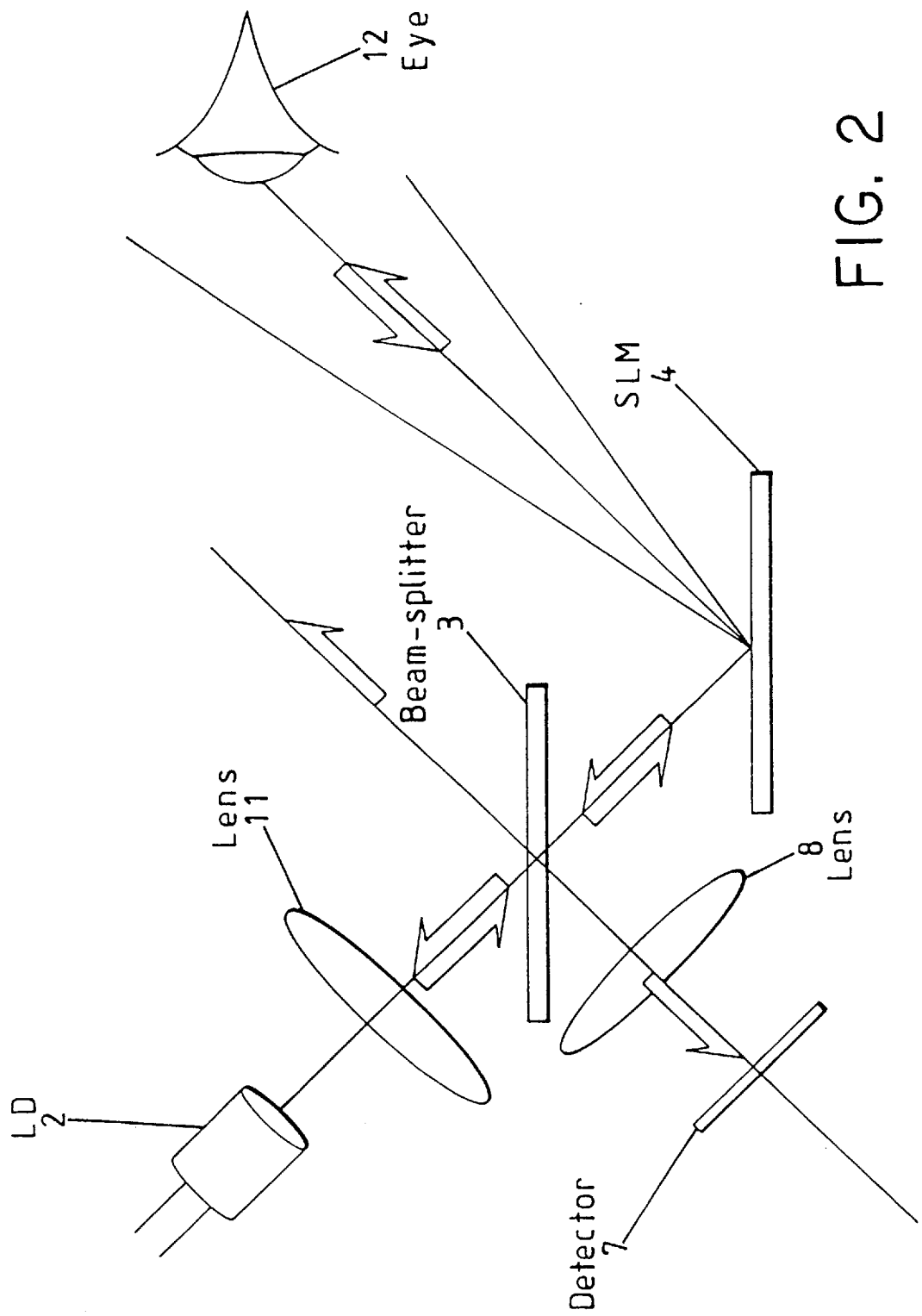
FIG. 2 illustrates diagrammatically part of the optical system shown in FIG. 1.

The optical system of the arrangement shown in FIG. 1 is shown in more detail in FIG. 2. The laser diode 2 produces a collimated beam of infrared radiation of finite area which is focused by a lens 11 through the beam splitter 3 into a spot on the SLM 4. The size of the beam determines the size of the spot such that larger beams produce smaller focused spots on the SLM 4. Diffraction patterns are written into the portion of the SLM 4 on which the spot is incident so as to perform beam deflection. The finite spot incident on the SLM 4 covers, for instance, an array of N×N independent picture elements (pixels) which allows angular deflection of the beam to N×N angles in two dimensions by writing the appropriate patterns on the SLM. By virtue of diffraction, beams from neighbouring discrete angles overlap so that the output beam from the SLM 4 can be scanned over the whole space within the maximum angle allowed, which maximum angle is determined by the pixel pitch of the SLM 4.

When the eye 12 is illuminated by the scanned output beam, it acts as a retro-reflector. The reflected divergent beam is incident on the whole surface of the SLM 4, which carries replicated N×N patterns, Thus, the whole SLM 4 acts as a deflector or mirror with the same deflection angle as the N×N area but with greater resolution, The retro-reflected infrared beam from the eye thus returns along the path of the illuminating beam to the beam splitter 3 and is reflected towards the lens 8. The lens 8 forms the Fourier transforms at its focal plane where the detector 7 is located.

The position sensitive detector 7 is of known type, for instance Sharp PSD # PD 3101F, and provides the cartesian coordinates of the centre of illumination of the image formed on the detector surface. This position together with the known geometry and deflection angle produced by the SLM 4 determine the direction of the centre of the pupil of the eye 12 with respect to the system.

The use of repeated patterns on the SLM 4 allows the SLM to be updated with fresh deflection patterns relatively quickly. Although this limits the number of discrete deflection angles compared with using the whole area of the SLM to define more narrow output beam positions, the SLM 4 may be updated sufficiently quickly to permit real time scanning using practical SLM technology. The loss in resolution caused by the limited resolution of scanning is compensated by the use of the position sensitive detector 7, which produces the coordinates of the centre of illumination very quickly.

Figure 3:
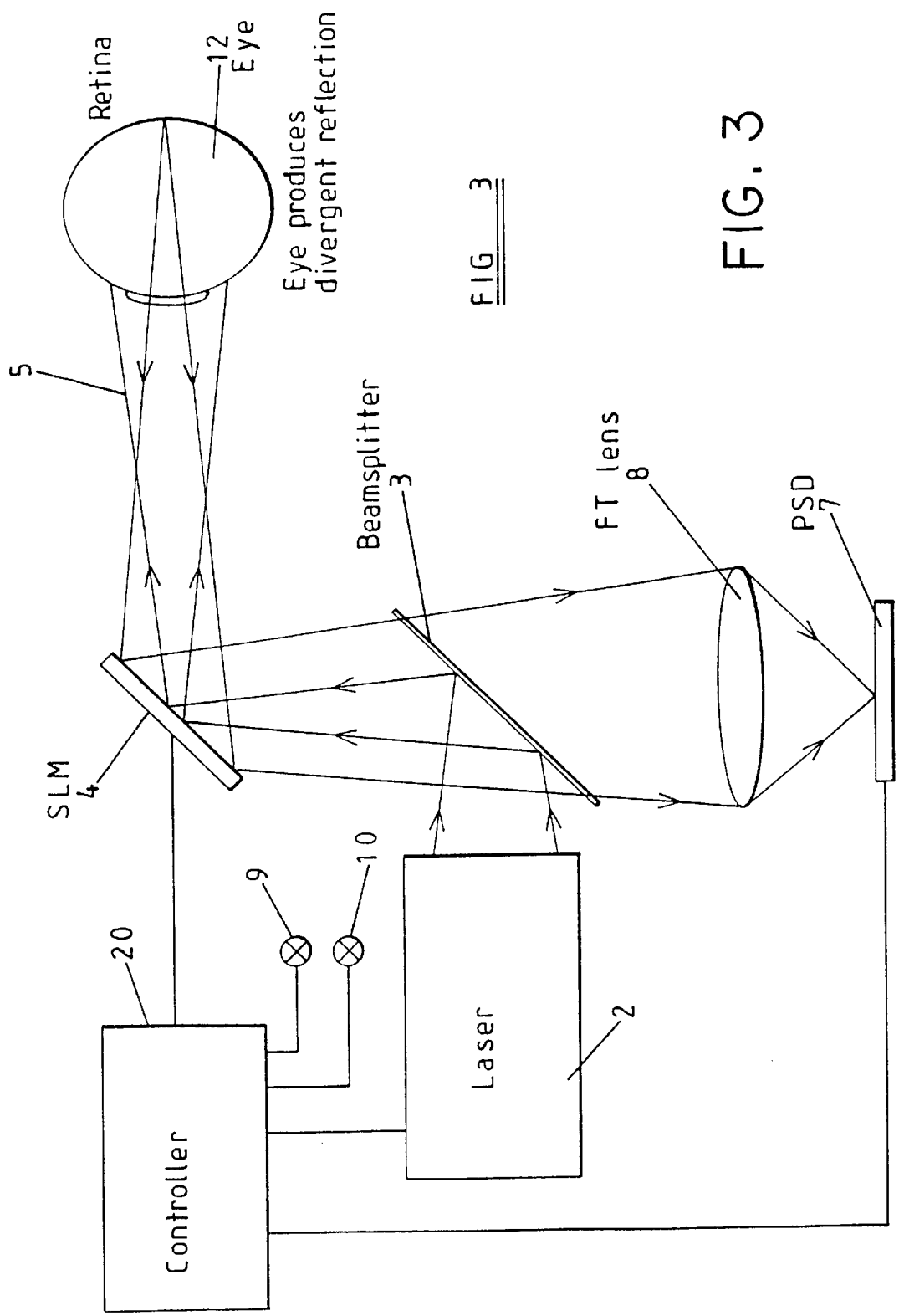
FIG. 3 illustrates diagrammatically beams produced by the system of FIG. 1.

FIG. 3 illustrates diagrammatically the beams produced when the scanning beam is incident on the eye 12. The laser 2, the SLM 4, the position sensitive detector 7 and the sources 9 and 10 are connected to a controller 20 which controls operation as follows.

Before detection of the eye 12 of the observer, the laser 2 is switched on and a first reflected pattern is written to the SLM 4, This causes the divergent scanning beam 5 to be diffracted at a predetermined angle associated with the replicated pattern. The output of the detector 7 is monitored for the presence of retro-reflection from the eye 12 If such reflection is not detected, a fresh replicated pattern is written to the SLM 4 so that the beam 5 is deflected to a different angle. This process continues with the scanning beam 5 being deflected to a plurality of overlapping beam areas so that the whole region in front of the screen 1 where an observer eye might be located is scanned.

When the detector 7 detects a retro-reflection from the eye 12, scanning by the SLM 4 is stopped so that the beam 5 remains directed at the eye 12. If necessary or desirable, a new replicated pattern may be written to the SLM 4 so that the retro-reflection is substantially centred on the detector 7. The controller 20 then calculates the direction to the centre of the pupil from the deflection angle produced by the SLM 4 and the position of the centre of illumination of the retro-reflection on the detector 7.

The diffraction pattern on the SLM 4 is maintained and the laser 2 is switched off. The infrared source 9 is then illuminated and the glint from the cornea of the eye 12 is imaged onto the detector 7 which supplies the coordinates of the centre of the illumination of the glint on the detector The controller 20 calculates the direction of the glint from these coordinates and from the deflection angle of the SLM 4. The source 9 is switched off and the process is repeated with the source 10 switched on so as to determine the angle of the glint caused by illumination of the source 10. The controller 20 then derives from these angles the region of the screen 1 at which the observer is gazing.

These measurements are repeated without changing the deflection produced by the SLM 4 for as long as the eye 12 remains within the beam 5. Small movements of the eye may be tracked, for instance by altering the replicated pattern on the SLM 4 to maintain the image of the retro-reflection on the detector 7. For instance, when the controller 20 detects movement of the retro-reflected image on the detector 7, the replicated pattern on the SLM 4 may be adjusted so as to scan the beam 5 such that it remains directed at the eye 12 with the retro-reflection centred as far as possible with respect to the detector 7. If the eye 12 moves such that the retro-reflected image is lost, the controller may start scanning the beam 5, for instance by choosing beam deflection angles around the last angle at which the eye was detected. If such tracking fails, then the controller may begin a new cycle of operation as described hereinbefore to locate the eye.

Figure 4:
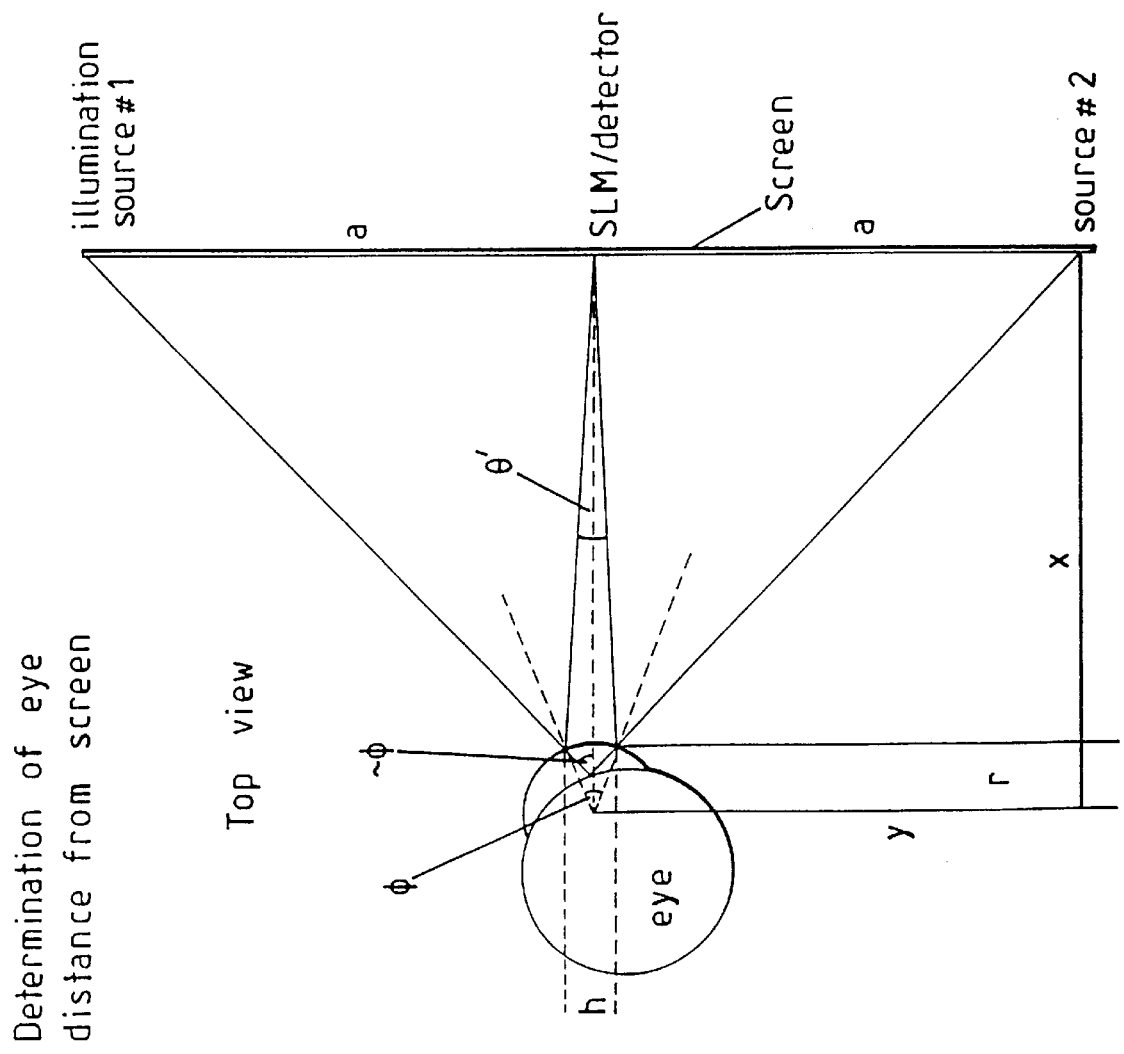
FIGS. 4 to 6 illustrate calculation of gaze position using the system shown in FIG. 1.
Figure 5:
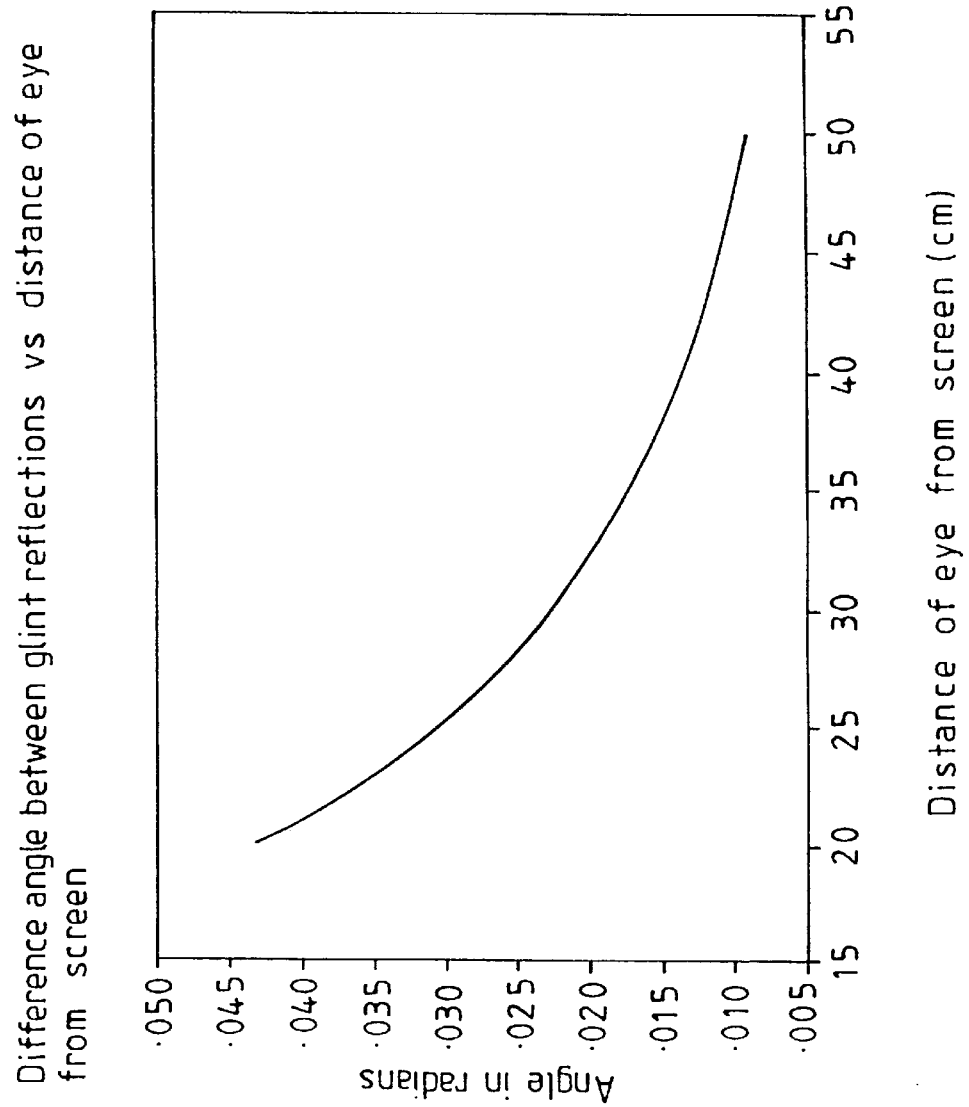

The system uses the position of the pupil and glint of the eye to determine gaze. The resolution therefore depends on the accuracy with which the angles of the reflections from the pupil (the retro-reflection) and the cornea (the glint) can be determined. By way of example, FIG. 4 shows an approximate one-dimensional calculation determining the position of the eye from the screen Such a calculation may be performed by a data processor within the controller (20). The diagram represents the top view of an eye situated directly in front of the screen at a distance x, where h is the distance between the glints caused by the first and second sources 9, 10, $\phi$ is the angle subtended by the glints and a point at the retina on a notional line corresponding to the bisection of the distance between the glints on the retina, and $\theta'$ is the angle subtended by the glints and the perpendicular intersection of the notional line at surface of the screen. Illumination occurs from both sides of the screen and the scanned beam using the SLM4, The calculation is carried out in 1D and assumes only information from the reflection of the peripheral light sources This is sufficient for an estimation of the 2D resolution. FIG. 5 shows the relationship obtained from the above calculation shown in FIG. 4 between the distance of the eye and the measured difference angle between the reflections from the first and second sources 9, 10.

The angular resolution of the SLM4 is limited by the size of the SLM by diffraction and can be described by:

$$\Delta\theta' \approx \frac{\lambda}{D},$$

where D is the dimension of the SLM, and $\lambda$ the wavelength of the illumination. For the following typical values for the parameters: x ~50 cm, r~1 cm, a~25 cm, $\lambda$~1 $\mu$m, and D~1 cm, the typical accuracy to which the distance of the eye could be determined from the screen using this technique is:

$$|\Delta x| \approx 0.2 \text{ mm}$$

Figure 6:
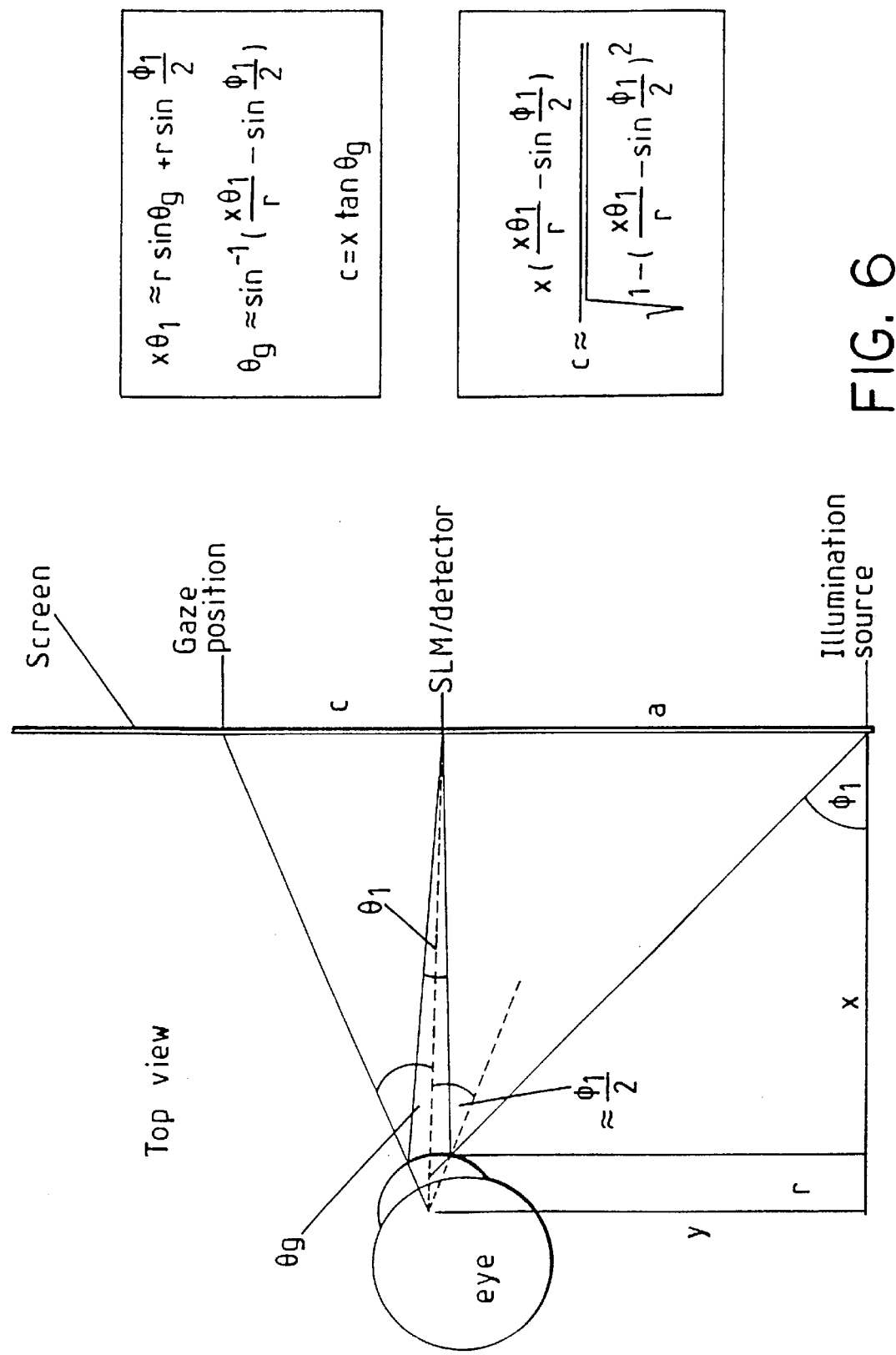

Once the distance of the eye from the screen is obtained, then the gaze angle can be inferred from one glint spot and the retro-reflected red-eye spot. The former gives the position of the surface of the cornea and the latter the position of the pupil within the cornea. Schematically the optical beams are shown in FIG. 6. From geometrical considerations, the position of the point on the screen at which the eye is looking can be obtained and is given by:

$$c \approx \frac{x\left(\frac{x\theta_1}{r} - \sin\frac{\phi_1}{2}\right)}{\sqrt{1 - \left(\frac{x\theta_1}{r} - \sin\frac{\phi_1}{2}\right)^2}} = \frac{x\sin\theta_g}{\cos\theta_g}$$

Differentiating this expression with respect to the measured angle gives an expression for the error in c for given errors in $\theta_g$. That is:

$$|\Delta c| \approx x \sec^2\theta_g \Delta\theta_g - \tan\theta_g \Delta x$$

where further differentiation of the expression for the gaze angle in terms of the measured angle as given in FIG. 6 yields:

$$\cos\theta_g \Delta\theta_g = \frac{x}{r}\Delta\theta_1 + \frac{\theta_1}{r}\Delta x$$

Combining these equations, the following expression for the error in the viewing point related to angular and distance measurement error can be obtained:

$$|\Delta c| \approx \frac{x^2 \sec^3\theta_g}{r}\Delta\theta_1 + \frac{x\sec^3\theta_g\theta_1}{r}\Delta x - \tan\theta_g \Delta x$$

Substituting the typical values given above and assuming $\theta_1$~r/x, and $\theta_g$~25°, the positional accuracy of the eye gaze position can be estimated at 0.5 mm for the described system limited only by diffraction.

The above calculations indicate roughly the theoretical best case accuracy of the system. However, the extent to which diffraction limited performance can be approached is dependent on the optical quality of the sources and optical elements of the system. In practice, a more iterative method of determining the position of the eye and the gaze direction may be used to allow more accurate relative positioning to be determined more quickly. Such an iterative method may use a microprocessor-based numerical algorithm and may be based on precalibration of the observer eye. For example, the observer may track a calibration image on the screen and the eye position measurements may be made as described hereinbefore. These measurements may be used during the precalibration to alter or adapt the algorithm in accordance with the specific properties of the observer eye.

Other embodiments include optical discrimination of reflected signals by using for example the polarisation characteristics of the reflected waves. Specular reflections from elements such as the cornea or glass optics in front of the eye could possibly be discriminated against by realising that such reflections preserve polarisation. Using a polarised laser diode source and a polariser to analyse the reflected beam, such erroneous reflections can be suppressed with regard to the unpolarised retro-reflected beam. Another means of discrimination could use multiple laser sources of varying wavelength and only detecting certain wavelengths for different reflections. For example, when originally searching for the eye, the scanning beam could consist of two wavelengths whose ratio in reflection could be tuned to the relative retina reflection coefficients. Subsequent detection and analysis of the reflected intensities of the two wavelengths (possibly using separate detectors behind optical filters) should improve the confidence with which the eye is first detected. With this scheme and indeed the whole system, calibration to a user may be used in terms of optical performance of that user's eye.

What is claimed is:

1. An eye detection system comprising:
   a light source for emitting an incident beam of optical radiation,
   a controllable deflector disposed in the path of the incident beam and operative in combination with the light source for producing a divergent scanning beam, and
   a detector for detecting radiation reflected by an eye back along the path of the scanning beam.

2. A system as claimed in claim 1, wherein the deflector comprises a controllable diffractive element.

3. A system as claimed in claim 2, wherein the deflector comprises a spatial optical modulator.

4. A system as claimed in claim 3, wherein the deflector further comprises a modulator controller for writing in the modulator an array of A×B substantially identical patterns, each of which comprises an array of C×D picture elements, where A, B, C and D are integers.

5. A system as claimed in claim 4, wherein the modulator controller is arranged to select each of the identical patterns from (C×D) different patterns for deflecting the scanning beam in (C×D) different directions.

6. A system as claimed in claim 5, wherein each of the different patterns is arranged to produce divergence in the scanning beam.

7. A system as claimed in claim 4, wherein the source is arranged to illuminate an array of C×D picture elements of the modulator with the incident beam.

8. A system as claimed in claim 1, wherein the detector is arranged to receive radiation deflected back towards the source by the deflector.

9. A system as claimed in claim 8, wherein a beam splitter for directing radiation from the source to the deflector and for directing radiation from the deflector to the detector.

10. A system as claimed in claim 8, wherein the detector comprises a detecting device disposed at the focus of a focusing optical system.

11. A system as claimed in claim 10, wherein the detecting device comprises a position sensitive detector.

12. A system as claimed in claim 10, wherein the focusing optical system comprises a converging lens.

13. A system as claimed in claim 1, wherein the source is arranged to produce a divergent incident beam.

14. A system as claimed in claim 13, wherein the source comprises a laser and the laser cooperates with a collimator and an aperture to produce the divergent incident beam.

15. A system as claimed in claim 1, wherein the source comprises a laser.

16. A system as claimed in claim 15, wherein the laser comprises a laser diode.

17. A system as claimed in claim 1, further comprising a scanning controller for causing the deflector to scan the scanning beam until the detector detects reflection from an eye.

18. A system as claimed in claim 17, wherein the scanning controller is arranged, after detection of reflection from the eye, substantially to center a center of reflection from the eye in the scanning beam or with respect to the detector.

19. A system as claimed in claim 1, comprising at least one further source of optical radiation disposed remotely from the deflector.

20. A system as claimed in claim 19, wherein the at least one further source is arranged to emit a divergent beam.

21. A system as claimed in claim 20, wherein the at least one further source comprises a laser and the laser cooperates with a collimator and an aperture to produce the divergent beam.

22. A system as claimed in claim 19, wherein the at least one further source comprises a laser.

23. A system as claimed in claim 22, wherein the at least one laser comprises a laser diode.

24. A system as claimed in claim 19, comprising a source controller for illuminating the source and the at least one further source in sequence.

25. A system as claimed in claim 24, wherein the source controller is arranged to illuminate each of the source and the at least one further source following detection by the detector of reflection from the eye of optical radiation from a previously illuminated one of the source and the at least one further source.

26. A system as claimed in claim 19, comprising a data processor for cooperating with the detector and the deflector to determine, from the angle between a predetermined direction and the direction from the deflector to the point of reflection at the eye of each of the source and the at least one further source, the eye gaze point on a surface in front of the eye.

* * * * *